(12) United States Patent
Phillips

(10) Patent No.: US 6,736,775 B2
(45) Date of Patent: May 18, 2004

(54) RETRACTOR CLAMP ASSEMBLY

(75) Inventor: Burns P. Phillips, Nashville, TN (US)

(73) Assignee: Boss Instruments Limited, Nashville, TN (US)

( * ) Notice: Subject to any disclaimer, the term of this patent is extended or adjusted under 35 U.S.C. 154(b) by 188 days.

(21) Appl. No.: 10/154,669

(22) Filed: May 23, 2002

(65) Prior Publication Data

US 2002/0177754 A1 Nov. 28, 2002

Related U.S. Application Data

(60) Provisional application No. 60/293,057, filed on May 23, 2001.

(51) Int. Cl.[7] ............................................... A61B 17/60
(52) U.S. Cl. ......................................... 600/234; 606/57
(58) Field of Search ................................ 600/228, 230, 600/231, 233, 234; 606/57

(56) References Cited

U.S. PATENT DOCUMENTS 6,616,664 B2 * 9/2003 Walulik et al. ............... 606/57

* cited by examiner

Primary Examiner—Cary E. O'Connor
Assistant Examiner—Candice C. Melson
(74) Attorney, Agent, or Firm—Stephen J. Stark; Miller & Martin PLLC

(57) ABSTRACT

A clamping device, preferably for use on a retractor support, has an upper clamp and a lower clamp. The clamps include a movable jaw and a fixed jaw pivotal between a locked configuration and an unlocked configuration which both locks the clamps in a shut configuration and fixes the angular position of the clamps relative to one another. A drawbar and cam act together to compress the upper and lower clamps into a clamping or locking position.

21 Claims, 3 Drawing Sheets

RETRACTOR CLAMP ASSEMBLY

This application claims the benefit of U.S. Provisional Application No. 60/293,057 filed May 23, 2001.

FIELD OF THE INVENTION

The present invention relates to surgical retractor support devices and, more particularly to a multi-position clamping mechanism for a surgical retractor.

BACKGROUND OF THE INVENTION

In surgery that requires access to internal structures, retractors are often used to hold back tissue and expose the area in which the surgical operation is to be performed. A retractor typically includes a retractor blade and a retractor shaft upon which the retractor blade is mounted. The retractor is attached to a retractor support by a clamping device. The retractor support includes a rod which the retractor clamp can engage to connect the retractor to the retractor support.

An essential feature of any retractor clamp is that the clamp allow the retractors to be conveniently positioned on the retractor support and be adjustable as necessary to achieve appropriate positioning with respect to the area of surgical operation.

Various types of clamping devices have been proposed. Minnesota Scientific, Inc. is the assignee of U.S. Pat. Nos. 4,949,707, 5,020,195, 5,025,780, 5,242,240, 5,727,899, and 5,792,046, which are incorporated by reference. These patents relate to various improvements to the basic concept of holding two rod sections in an adjustable and fixable angular relationship relative to one another when locked in position. One of the rod sections is usually a retractor handle and the other is usually a rod section of a retractor support, which may be mounted to the operating table or other appropriate location.

Although, these clamping devices are believed to operate satisfactorily (i.e., to clamp two rod sections in a specific angular relationship), a need exists to provide the ability for at least one of the two rod sections to "snap" into a loosely gripped position to allow for precise positioning off the rod relative to the clamp before "clamping" the clamp into a securely locked position which prevents either of the two rod sections from moving relative to one another.

A need also exists to provide jaws for clamping members, which operate about pivot points to provide a scissors-like gripping action.

Furthermore, although the frustro-conical section provided in U.S. Pat. No. 4,949,707 provides one way to provide a large amount of surface area to resist twisting of the clamping members relative to one another when locked, an improvement is needed to securely position the two clamping members relative to one another in a locked position.

SUMMARY OF THE INVENTION

The retractor clamp preferably includes a drawbar extending at least partially through two clamping members which are rotatable relative to one another. The clamping members are comprised of a stationary jaw and a jaw movable about respective pivot points upon activation of a connected lever arm. The draw bar has an opening at its distal end for holding a dowel. The dowel fits within a cam nut such that when the draw bar is turned the cam activates the lever arms locking the clamps in a closed position.

A spring located in the lower clamping member biases the moveable arms such that the first and second jaws are biased to "snap" about an inserted rod section.

The two clamping members are separated by a lock bushing having a top disc and a bottom disc. The lock bushing has a preload spring between the top and lower disc. When the cam is not activated the preload spring prevents the top bushing and the lower bushing from engaging. This allows the two clamping members to rotate freely with respect to one another.

Additionally, the lock bushing top and bottom discs adjoin one another along cooperating serrations. The cooperating serrations engage one another when the drawbar is turned sufficiently to activate the cam, thereby locking the first and second clamping members in a fixed angular relationship relative to one another.

BRIEF DESCRIPTION OF THE DRAWINGS

The particular features and advantages of the invention as well as other objects will become apparent from the following description taken in connection with the accompanying drawings in which:

FIG. 3b is a side-on view of the cam nut of FIG. 3a;

DETAILED DESCRIPTION OF THE PREFERRED EMBODIMENT

Figure 1:
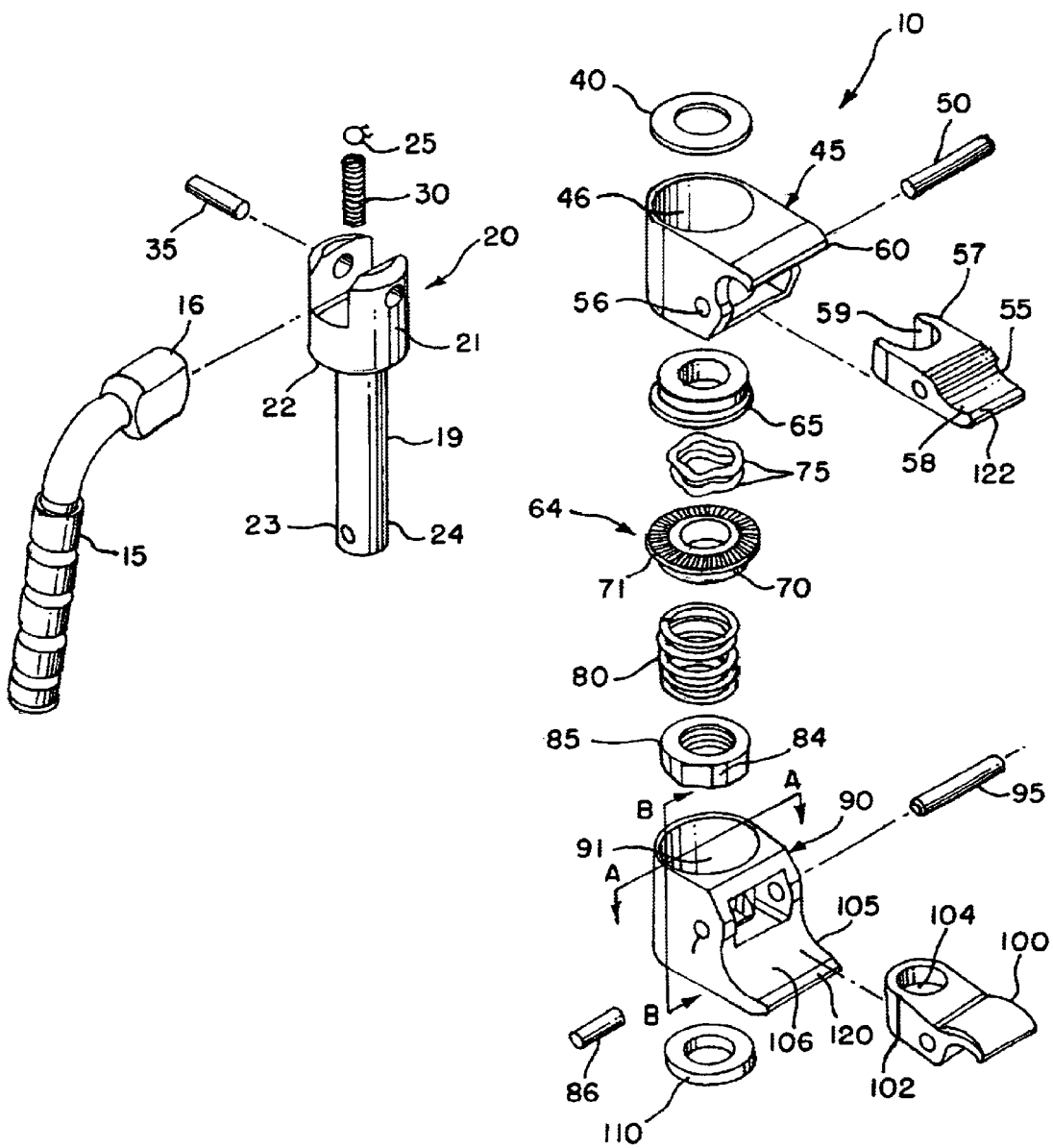
FIG. 1 is an exploded perspective view of the clamp of the preferred embodiment of the present invention.

The retractor clamp 10 of FIGS. 1–4 may be utilized as a replacement for or instead of the clamp illustrated in FIG. 1 of U.S. Pat. No. 5,020,195. However, the clamp 10 of the present preferred embodiment is believed to improve on the basic design of that prior art retractor clamp and others.

The clamp 10 of FIG. 1 is comprised of two clamping members 45, 90 with each having at least one moveable jaw member 55, 100, respectively. The moveable jaw members 55, 100 preferably rotate about respective pivots 56, 101 when forces are exerted on lever arms 57, 102 which are located opposite the pivot points 56, 101 at moveable jaws 55, 100. The moveable jaw members 55, 110 are pivotably connected to the clamping members 45, 90 by upper clamp dowel 50 and lower clamp dowel 95, respectively.

In the preferred embodiment, each of the moveable jaws 55, 100 cooperates with a second jaw member 60, 105, which is preferably a fixed, or non-moving jaw member. In a more preferred embodiment, the fixed jaw members 60, 105 are of unitary construction with a significant portion of the upper and lower clamps 45, 90 respectively. The fixed jaw members 60, 105 have a gripping surface 61 (obscured from view on jaw member 60) and 106 which cooperate with gripping surfaces 58 and (obscured from view on jaw 100) of the moveable jaw members 55, 100 to hold rod sections such as a shaft of a retractor and a rod section of a retractor support. The jaw faces such as gripping surfaces 106, 58 are preferably curved to aid in holding the rod sections once they are in place.

Figure 5:
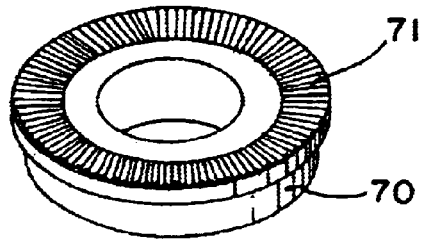
FIG. 5 is a perspective view of the lock bushing disc.

The clamping members 45, 90 are separated by a bushing such as lock bushing 64. The lock bushing 64 consists of top lock 65 and lower lock 70. The locks 65, 70 illustrated as disks are preferably constructed with serrated interfaces 71, as best seen in FIG. 5, which cooperate with one another to maintain the upper clamp 45 in a fixed radial position relative to the lower clamp 90 when the clamping members 45, 90 are locked, at least angularly, relative to one another. The serrated interfaces 66, 71 in the preferred embodiment resemble a starburst type shape characterized by radially extending ridges. The upper and lower discs 65, 70 are separated by pre-load spring 75. The pre-load swing 75 keeps the serrated interfaces 71 from contact when the clamping members 45, 90 are in an unlocked or release position. The spring 75 therefore assists in the free rotation of the clamping members 45, 90.

In the preferred embodiment, a drawbar 20 is utilized to operate the moveable jaws 55, 100 and to lock the upper and lower clamping members 45, 90 in a fixed angular relationship relative to one another. The drawbar 20 extends through bores 46, 91 in the clamping members 45, 90. The drawbar 20 also extends through channels 59, 104 in lever arms 57, 102.

Figure 2:
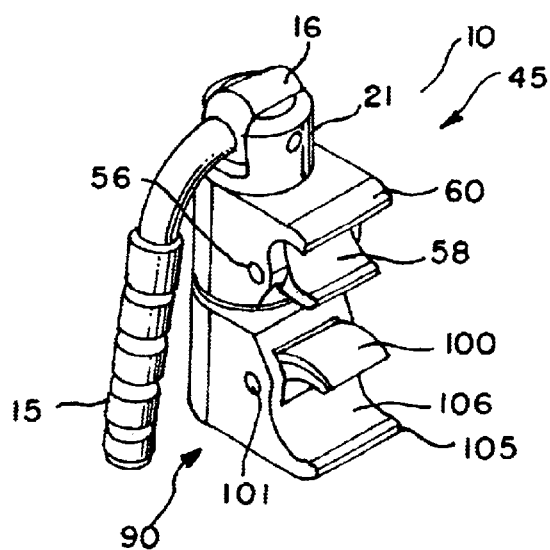
FIG. 2 is a perspective view of the clamp of FIG. 1.

The drawbar 20 may be rotated within clamping members 45, 90 by handle 15. The handle 15 or gripping surface is positioned to receive handle ball 25 as shown in FIG. 2. Handle spring 30 biases the handle ball into the handle 15. When handle 15 is raised it pivots around handle dowel 35 while maintaining contact with ball 25. The handle ball 25 is preferably received within a recess (obscured from view) in base 16 of handle 15 when the handle 15 is pivoted to be substantially perpendicular to the drawbar 20. When the handle 15 is released the handle spring 30 may assist to bias the handle to a closed position as shown in FIG. 2.

The drawbar 20 has drawbar head 21 with lip 22, which rests on washer 23, such as a friction washer. The drawbar head 21 when turned rotates on the washer 23, which abuts lever arm 57. The turning of the drawbar drives the drawbar head 21 downward applying sufficient downward forces on the lever arm 57 with the lip 22 to actuate a closed or clamping position as will be explained in further detail below.

Figure 3A:
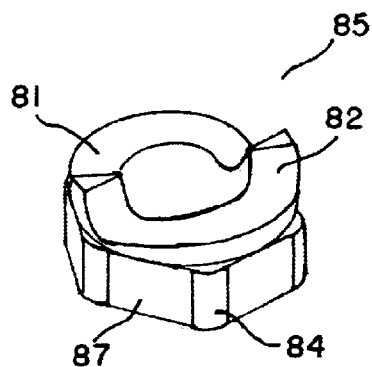
FIG. 3a is a perspective view of a cam nut shown in FIG. 1.

The drawbar 20 is secured within the clamping members 45, 90 by a cam illustrated as a cam nut 85, best seen in FIG. 3a. Cam nut 85 is engineered to receive cam nut dowel 86, which extends from the hole 23 in the distal end 24 of the drawbar shaft 19. The cam nut dowel 86 is positioned to fit within the cam nut 85 such that when the drawbar 20 is turned the nut dowel 86 moves relative to the cam nut 85.

Figure 3B:
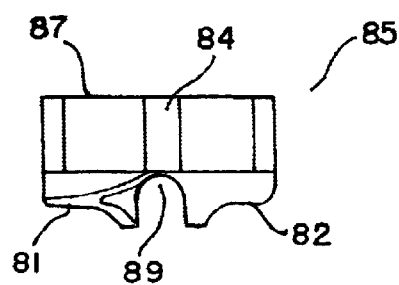

The shape of the cam nut 85 may be any shape that allows it to be housed within the lower clamp 90 so that the cam nut 85 preferably will not rotate when the drawbar 20 is rotated. Referring to FIG. 3a, the cam nut 85 is illustrated upside down in a preferred embodiment showing three sides of a hexagonal nut base 87 with each side having a turret 84. FIG. 3a further illustrates the cam portions 81, 82. FIG. 3b shows the cam nut 85 as it is placed in the retractor clamp 10. Dowel channel 89 holds the cam nut dowel 86 and separates a first cam ramp 81 and a second cam ramp 82. When the drawbar 20 is turned the cam nut dowel 86 preferably rotates up both cam ramps 81, 82. As shown in FIG. 3b the cam dowel 86 can only turn in one direction, in this case clockwise, however the cam nut 85 can be constructed to turn in the opposite direction with equal effect. If the article to be gripped by the clamping members has a diameter too small to be gripped by the retractor clamp 10 the cam nut dowel 86 may ride over the cam ramps 81, 82 and fall back into the dowel channel 89.

Figure 4A:
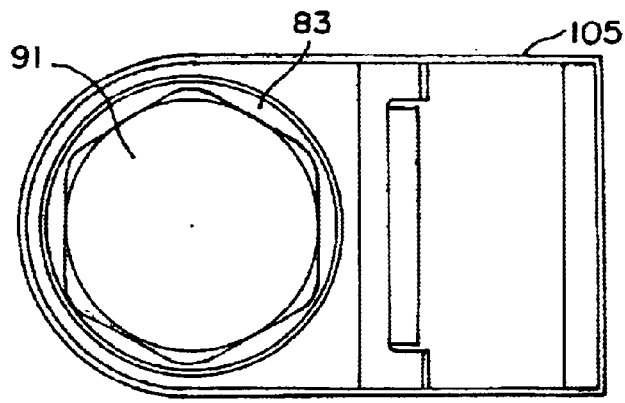
FIG. 4a is a cross-section view of a portion of the lower clamp as shown along the line A—A in FIG. 1.
Figure 4B:
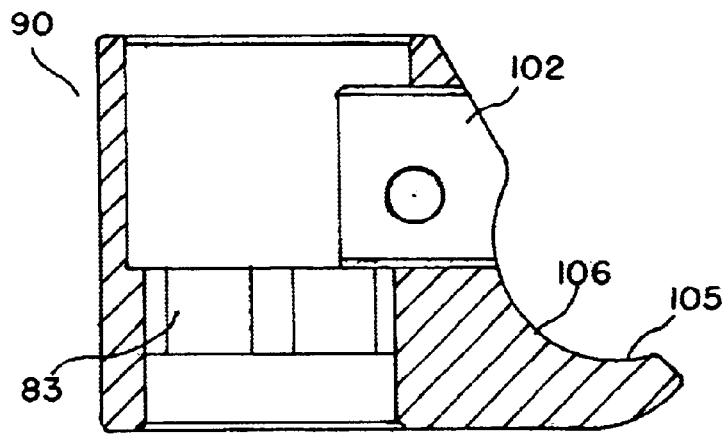
FIG. 4b is a cross-section view taken along line B—B of the lower clamp in FIG. 1.

Referring back to FIG. 1, the cam nut 85 is supported from below by cam nut dowel 86 and is prevented from upward vertical movement by the compression spring 80, which presses against the cam nut 85 and the lever arm 102. The cam nut 85 is prevented from rotating or lateral movement by cam nut housing 83 located in the interior of lower clamp 90 as shown in FIG. 4a. The hexagonal shape of the cam nut housing 83 of the lower clamp 91 is shown in this figure. The shape of the cam nut housing 83 has been designed to accept the cam nut turrets 84 of the cam nut 85 thereby preventing the cam nut 85 from rotating in the lower clamp bore 91.

The compression spring 80 positioned between the cam nut 85 and lower clamp moving jaw 100 preferably performs the dual function of biasing the lever arm 102 to a static clamping position thereby placing the clamp 90 in a shut configuration, but not a locked configuration, i.e., when in an unlocked configuration, and biasing the cam nut 85 to the cam dowel 86 such that when the cam dowel 86 is turned a predetermined amount, the spring 80 is compressed further tightening the upper and lower clamps 45, 90 into a locked configuration. Accordingly, when inserting a rod to be fixed by the lower clamp 90, the rod may be pushed into the clamping member 90 so that it "snaps" into position even while the retractor clamp 10 is in an unlocked configuration loading surfaces 120, 122 on jaws 55, 105 may also be present on jaws 60, 100 to assist in spreading the jaws 55, 60 and 100, 105 upon insertion of a rod (i.e., the curved surface of the rod would spread the jaws apart until the diameter was reached, and the jaws would come back together about the rod.) The lower clamp moving jaw 100 is biased downward by the spring 80 since the spring 80 pushes upward on the lever arm 102 forcing moving jaw 100 downward toward the fixed jaw 105. The force exerted by the compression spring 80 is preferably sufficient to secure the retractor clamp 10 to a rod.

After the lower clamp 90 has been placed into position the drawbar 19 can be turned which turns the cam dowel 86. This movement causes the dowel 86 to ride up the cam ramps 81, 82 compressing spring 80 and moving or exerting upward force on the lever arm 102 and places the clamp 90 in a locked configuration. The upward force on lever arm 102 provides additional grip to further secure a rod section.

In order to lock the upper clamp 45 about a rod section the drawbar 20 may be rotated, such as by handle 15 by the same rotation that locks clamp 90. In the preferred embodiment, less than 270 degrees, and less than 180 degrees of rotation have each been found satisfactory to lock the clamping members 45, 90 about a rod section. Once again the rotating action of the handle 15 causes the cam nut dowel 86 to turn and ride up the cam ramps 81, 82. This motion pulls the draw bar head 21 down and forces the lip 22 to place pressure on the friction washer 40, which in turn pushes down on lever arm 57 into a locked configuration. Lever arm 57 pushes moving jaw 55 upward and toward the fixed jaw 60 until the upper clamp 45 has secured the inserted rod section.

Another effect associated with the downward force applied by the drawbar head 21 and/or action of the drawbar 20 with the cam nut 85 is the compression of the pre-load spring 75 in lock bushing 64. This forces the serrated disc faces 71, 66 to contact one another and cooperate with one another to maintain the upper clamp 45 in a fixed radial position relative to the lower clamp 90 in a locked configuration. Rotation can be reestablished by turning the drawbar 19 in the opposite direction riding the cam dowel 86 back down the cam ramps 88. While a single drawbar 20 and cam nut 85 are utilized to lock and unlock the clamps 45, 90 and the bushing 64, a plurality of similar or dissimilar mechanisms could be utilized in other embodiments.

Numerous alterations of the structure herein disclosed will suggest themselves to those skilled in the art. However, it is to be understood that the present disclosure relates to the preferred embodiment of the invention, which is for purposes of illustration only and not to be construed as a limitation of the invention. All such modifications, which do not depart from the spirit of the invention, are intended to be included within the scope of the appended claims.

What is claimed is:

1. A surgical clamp apparatus comprising:
   a first clamp having first and second jaws pivotally attached to each other;
   a second clamp having first and second jaws pivotally attached to each other, said second clamp connected to the first clamp and rotatable relative to the first clamp in an unlocked configuration;
   first and second serrated locks located between the first and second clamp, wherein said first serrated lock is connected to the first clamp and the second serrated lock is connected to the second clamp;
   wherein the serrated locks are in contact with one another thereby fixing the angular relationship of the first clamp relative to the second clamp in a locked configuration, and
   the serrated locks are spaced apart from one another in the unlocked configuration allowing the second clamp to rotate relative to the first clamp.

2. The surgical clamp apparatus of claim 1 further comprising a spring biasing the first and second serrated locks into the unlocked configuration.

3. The surgical clamp apparatus of claim 2 wherein the spring is located intermediate portions of the first and second locks.

4. The surgical clamp apparatus of claim 1 wherein the first jaw of the first clamp is connected to a lever arm and a pivot point, the pivot point located intermediate the lever arm and the second jaw.

5. The surgical clamp apparatus of claim 4 wherein the first jaw of the second clamp is connected to a lever arm and a pivot point, the pivot point located intermediate the lever arm and the second jaw.

6. The surgical clamp apparatus of claim 1 wherein the first and second clamps further comprise bores and have a drawbar extending at least partially through the bores of the first and second clamps and through the first and second serrated locks.

7. The surgical clamp apparatus of claim 6 further comprising a cam operably coupled to the drawbar wherein movement of the drawbar a predetermined amount relative to the cam switches the apparatus from the unlocked to the locked configuration.

8. The surgical clamp apparatus of claim 1 further comprising a spring normally biasing at least one of the first and second clamps in a closed position in the unlocked configuration.

9. A surgical clamp apparatus comprising:
   a first clamp member having a first jaw and a second jaw pivotable at a pivot point relative to the first jaw, said first clamp having a bore extending therethrough, said second jaw connected to a first lever arm with a pivot point intermediate the first lever arm and the second jaw, said first lever arm having a channel therethrough;
   a second clamp member having a first jaw and a second jaw pivotable relative to the first jaw, said second clamp having a bore extending at least partially therethrough, said second jaw connected to a second lever arm with a pivot point intermediate the second lever arm and the second jaw, said lever arm having a channel therethrough;
   a drawbar extending through the bore of the first clamp and through the channel of the leg of the first clamp and at least partially into at least one of the bore of the second clamp and the channel of the leg of the second clap, said drawbar having a proximal end with a head and a distal portion, said head having a gripping surface connected thereto; and
   a cam configured to cooperate with the distal portion of the drawbar, wherein movement of the drawbar from an unlocked configuration to a locked configuration moves the cam from an unlocked configuration to a locked configuration with said cam member moving toward the proximal end of the drawbar and securing the second lever arm and the second clamp in a locked configuration.

10. The surgical clamp apparatus of claim 9 wherein the first clamp is rotatable relative to the second clamp in the unlocked configuration.

11. The surgical clamp apparatus of claim 10 wherein an angular relationship of the first clamp relative to the second clamp is fixed in the locked configuration.

12. The surgical clamp apparatus of claim 11 wherein the first clamp further comprises a first serrated lock and the second clamp further comprises a second serrated lock, said first and second serrated locks spaced apart from each other in the unlocked configuration and in contact with one another in the locked configuration.

13. The surgical clamp apparatus of claim 9 wherein the drawbar extends at least through one of the bore of the second clamp and the channel of the leg of the second clamp.

14. The surgical clamp of claim 9 further comprising a spring biasing at least one of the first and second clamps in a closed configuration when the apparatus is in an unlocked configuration.

15. The surgical clamp of claim 14 wherein at least one of the first and second jaws of the second clamp further comprises a loading assist surface.

16. A surgical clamp apparatus comprising:
   a first clamp having a first jaw and a second jaw pivotable at a pivot point relative to the first jaw, said first clamp having a bore extending therethrough, said second jaw connected to lever arm opposite a gripping surface about the pivot point;
   a second clamp connected to the first clamp member; and
   wherein said first clamp member is spring biased into a closed configuration in an unlocked position, and locked in the closed configuration in a locked configuration.

17. The surgical clamp apparatus of claim 16 wherein at least one of the first and second jaws of the first clamp has a load assist surface.

18. The surgical clamp apparatus of claim 16 wherein the second clamp member is spring biased in a shut configuration in the unlocked position.

19. The surgical clamp apparatus of claim 16 further comprising a drawbar and a cam, and wherein the first and second jaws of the first and second clamps are connected at pivot points, said pivot points located intermediate the drawbar and the first and second jaws of the first and second clamps, respectively.

20. The surgical clamp apparatus of claim 19 wherein rotation of the drawbar relative to the cam a predetermined distance transitions the clamp apparatus from an unlocked to a locked configuration.

21. The surgical clamp apparatus of claim 16 further comprising a first serrated lock connected to the first clamp and a second serrated lock connected to the second clamp.

* * * * *